(12) United States Patent
Zhou et al.

(10) Patent No.: US 9,308,468 B2
(45) Date of Patent: Apr. 12, 2016

(54) INTEGRATED SYSTEM TECHNIQUE FOR COUPLING FIXED BED AND JET FLUIDIZED BED TO SEPARATOR UNIT

(75) Inventors: Zheng Zhou, Nanjing (CN); Zhibing Zhang, Nanjing (CN); Gaodong Yang, Nanjing (CN); Xionghui Gong, Nanjing (CN); Pingkeng Wu, Nanjing (CN)

(73) Assignee: NANJING UNIVERSITY (CN)

( * ) Notice: Subject to any disclaimer, the term of this patent is extended or adjusted under 35 U.S.C. 154(b) by 0 days.

(21) Appl. No.: 14/361,174

(22) PCT Filed: May 25, 2012

(86) PCT No.: PCT/CN2012/076045
§ 371 (c)(1),
(2), (4) Date: May 28, 2014

(87) PCT Pub. No.: WO2013/004111
PCT Pub. Date: Jan. 10, 2013

(65) Prior Publication Data
US 2014/0336407 A1    Nov. 13, 2014

(30) Foreign Application Priority Data
Jul. 7, 2011   (CN) .......................... 2011 1 01892765

(51) Int. Cl.
| | | |
|---|---|---|
| *B01D 3/00* | (2006.01) | |
| *B01J 8/08* | (2006.01) | |
| *B01J 8/02* | (2006.01) | |
| *C07C 29/48* | (2006.01) | |
| *C07C 67/297* | (2006.01) | |
| *B01J 8/00* | (2006.01) | |
| *B01J 19/18* | (2006.01) | |
| *C07C 67/08* | (2006.01) | |
| *C07C 29/04* | (2006.01) | |

(52) U.S. Cl.
CPC ................. *B01D 3/009* (2013.01); *B01J 8/005* (2013.01); *B01J 8/02* (2013.01); *B01J 8/08* (2013.01); *B01J 19/18* (2013.01); *C07C 29/04* (2013.01); *C07C 29/48* (2013.01); *C07C 67/08* (2013.01); *C07C 67/297* (2013.01); *B01J 2208/00557* (2013.01); *B01J 2219/0004* (2013.01); *B01J 2219/00006* (2013.01); *C07C 2101/16* (2013.01)

(58) Field of Classification Search
CPC ................ B01J 8/08; B01J 8/02; B01D 3/009
USPC ......................................................... 568/875
See application file for complete search history.

(56) References Cited

U.S. PATENT DOCUMENTS

| 7,232,936 | B1 | 6/2007 | Yurchak |
|---|---|---|---|
| 2010/0242361 | A1 | 9/2010 | Vail |

FOREIGN PATENT DOCUMENTS

| CN | 101684064 A | * | 3/2010 |
|---|---|---|---|
| WO | 03/070873 A2 | | 8/2003 |
| WO | 2013004111 A1 | | 1/2013 |

OTHER PUBLICATIONS

International Search Report; PCT/CN2012/076045; International File Date: May 25, 2012; Nanjing University 2 pgs.
Written Opinion; PCT/CN2012/076045; International File Date: May 25, 2012; Nanjing University; 7 pgs.
International Preliminary Report on Patentability; PCT/CN2012/076045; International File Date: May 25, 2012; Nanjing University; 8 pgs.

* cited by examiner

*Primary Examiner* — Yong Chu
(74) *Attorney, Agent, or Firm* — Schmeiser, Olsen & Watts, LLP

(57) ABSTRACT

A process of integrated system formed by coupling of fixed bed, jetting floating bed, and separating unit, aimed to provide a new process and equipment of higher efficiency, which integrates multi-type reactors and separation is provided. Reaction materials undergo preliminary reaction in fixed bed reactor and intensified reaction in jetting floating bed reactor, and then separation in the subsequent separation system. Unreacted materials will be returned to the raw material intermediate storage tank for mixing with fresh materials, as raw materials for continued reaction. During this process, materials first pass the fixed bed reactor once to achieve certain conversion rate, and then enter the jetting floating bed reactor for intensified reaction. When the product reaches required concentration, the materials will enter subsequent separation equipment for separation.

6 Claims, 1 Drawing Sheet

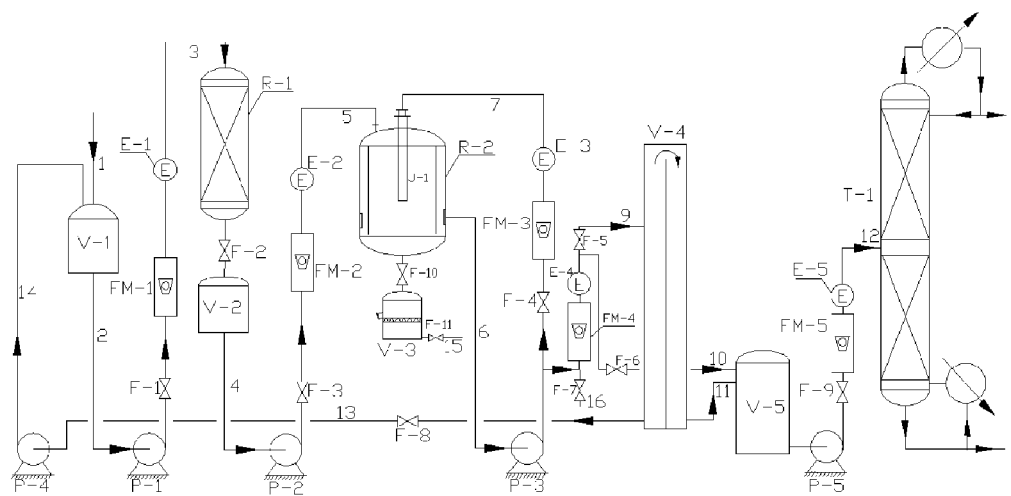

INTEGRATED SYSTEM TECHNIQUE FOR COUPLING FIXED BED AND JET FLUIDIZED BED TO SEPARATOR UNIT

CROSS-REFERENCE TO RELATED APPLICATIONS

This application claims priority to PCT Application No. PCT/CN2012/076045, having a filing date of May 25, 2012, based off of CN Application No. 2011101892765, having a filing date of July 7, 2011, the entire contents of which are hereby incorporated by reference.

FIELD OF TECHNOLOGY

This invention relates to an integrated process formed by coupling reactors of fixed bed and jet floating bed with a separating unit.

BACKGROUND

Fixed bed reactor is also referred to as packed bed reactor. It is filled with solid catalyst or solid reactant to realize heterogeneous reaction. The solid substance is normally in the form of particles, stacked to constitute a bed of certain height (or thickness). This bed is static and fluid flows through it for reaction. The difference between this reactor and fluidized bed reactor/moving bed reactor is that the solid particles are static. At present, liquid-solid catalytic reaction using solid catalyst and liquid reaction raw materials mainly adopts fixed bed reactor, e.g. esterification reaction and hydration reaction etc.

Advantages of fixed bed reactor: ① weak back-mixing, effective contact between fluid and catalyst, and relatively high selectivity in case the reaction is accompanied by side reaction in series; ② small mechanical loss of catalyst; ③ simple structure; ③ stable reaction. Disadvantages of fixed bed reactor: ① poor heat transfer; ② difficult replacement of catalyst during operation, hence not suitable for reactions that require frequent catalyst regeneration, which shall normally adopt fluidized bed reactor or moving bed reactor instead; ③ relatively low reaction efficiency; ④ difficult mixing of reactants involving two phases of materials, e.g. oil and water.

Jet floating bed reactor (JFBR) is a new type of intensified reactor. Its operating principle is use of high velocity mobile phase to suck other phases, generating intense stirring effect, promoting close contact among phases, and quickly completing the reaction. When used for liquid-solid catalytic reaction that adopts solid catalyst and liquid reaction raw materials, the JFBR allows full mixing of reactants and catalyst, greatly intensifies mass and heat transfer rate, improves concentration and temperature distribution inside reactor, accelerates reaction, effectively suppresses side reaction, and improves reaction selectivity.

JFBR has many unique outstanding performances: ① high mass transfer and heat transfer efficiency; ② high operation flexibility; ③ large input power per unit volume and low energy consumption; ④ simple reactor structure without rigid stirring, hence suitable for dangerous reactions such as oxidation and hydrogenation; ⑤ good sealing performance, in particular, suitable for high pressure system; ⑥ small effect of reactor scale on mixing effect and mass transfer rate, facilitating engineering amplification.

At present, industrial integrated reaction and separation system consists of reaction equipment and separation equipment combined together, and has certain defects. Examples include integrated fixed bed reaction-separation system, referred to as reaction rectifying tower, e.g. esterification reaction rectifying tower. Since relatively long reaction time is required to attain a relatively high conversion rate by means of fixed bed reactor, residence time is relatively long and equipment volume is relatively large. For other integrated reaction-separation systems, e.g. those consisting of oxidation or hydrogenation equipment and separating unit, the problem of difficult coupling between reaction and separation exists.

SUMMARY

The purpose of this invention is to provide a type of an integrated process coupling reactors of fixed bed and jet floating bed with separating unit, as shown in FIG. 1. In the reaction stage, a fixed bed reactor (FBR) is coupled to the JFBR. The FBR is used for preliminary reaction, followed by intensified reaction in the JFBR. The preliminary reaction in the FBR shortens the reaction time of intensified reaction in the JFBR, thus reduces solid catalyst broken and extends service life of solid catalyst. The JFBR can increase conversion rate of subsequent reaction in a relatively short time, with low energy consumption, thus making-up the disadvantages of long reaction time and low conversion rate of FBR. If the material flowing out of the reactor is delaminated, phase separator will be used to separate oil phase and water phase, with the phase containing product entering the rectifying system for separation; otherwise the material will directly enter the rectifying system, for timely removal of product and return of unreacted reactant to the reactors to increase conversion rate. This integrated process can greatly reduce energy consumption and cost.

The purpose of this invention can be realized by the following technical solution:

The process of the integrated process coupling reactors of fixed bed and jet floating bed with a separating unit, comprising the following steps:

Step 1: Input fresh reactants liquid required for the reaction (including all reactions suitable for the FBR) into the intermediate material storage tank V-1 via pipeline 1. Use raw the material transfer pump P-1 to quantificationally deliver these materials via the valve F-1, flowmeter FM-1, heat exchanger E-1 (for heating), and pipeline 3 to the fixed bed reactor R-1 for preliminary reaction. The reactants are then sent to the fixed bed reactor R-1 one time and be collected by the intermediate buffer tank V-2. The fixed bed reactor will be filled by required solid catalyst, the height and degree of finish of which shall be determined according to particular processing capacity and required residence time.

Step 2: Use the material transfer pump P-2 to deliver the reacted mixture of preliminary reaction in the FBR from the intermediate buffer tank V-2 to the JFBR R-2, via the valve F-3, flowmeter FM-2, heat exchanger E-2, and pipeline 5, for intensified reaction. The JFBR system consists of the main body of the reactor R-2, fluid transfer pump P-3, flowmeter FM-3, heat exchanger E-3, jet J-1, and corresponding pipelines and valves. The fluid from reactor R-2 is pumped into the jet J-1 by fluid pump P-3 through the valve F-4, flowmeter FM-3, heat exchanger E-3 (heating the fluid to the required temperature for the reaction) and pipeline 7. This fluid is finally injected back into reactor R-2 for cyclic intensified reaction. Particular dimensions of the JFBR R-2 shall be determined according to material processing capacity and residence time.

Step 3: After a period of reaction, take samples from the sampling port 16 for analysis. When the product reaches the specified concentration, the material will be output via the pipeline 9 or pipeline 10. In case the liquid phase of output mixture is delaminated, it will pass through the liquid flowmeter FM-4, heat exchanger E-4, valve F-5, and pipeline 9 to enter the phase separator V-4 for phase separation. The upper layer (oil phase) will enter the buffer tank V-5 via the pipeline 11. In case the liquid phase of output mixture is not delaminated, it will be directly pumped into the buffer tank V-5 via the valve F-6 and the pipeline 10.

Step 4: In case the liquid phase of the output mixture is delaminated, it will be separated into an oil phase and a water phase in the phase separator V-4. The liquid phase layer without objective product will be directly pumped into the raw material storage tank V-1 by the pump P-4 via the pipeline 13 and 14. The liquid phase containing objective product in the intermediate buffer tank V-5 will be sent to the separation unit for separation by the liquid pump P-5, valve F-9, liquid flowmeter FM-5, heat exchanger E-5 (heating the liquid to a desired temperature) and pipeline 12. In case the liquid phase of output mixture is not delaminated, the mixture containing product will be sent to the intermediate buffer tank V-5 through the liquid flowmeter FM-4, heat exchanger E-4 and valve F-6. Then the material will be further pumped by the liquid transfer pump P-5 to the separation unit T-1 for subsequent separation through the valve F-9, flowmeter FM-5, pipeline 12 and heat exchanger E-5 (heating the liquid to a desired temperature).

Step 5: In the separation unit T-1, products and unreacted materials will be separated by a packed/trayed column distillation unit and respectively collected. The products will be sent to the storage tanks for storage and the unreacted materials will be pumped back to the raw material intermediate storage tank V-1 for recycle.

In the above process of integrated system, the separation unit described in step 4 is equipped with a packed column distillation unit or a trayed column distillation unit. This invention has replenished and optimized traditional process of integrated system formed by coupling of single type reactor and separating unit. The reaction system described here includes all reaction systems that can adopt FBR. Preliminary reaction of reactants in the FBR is first carried out, followed by intensified reaction in JFBR. According to delamination of the material after reaction, this material is transferred to the separation unit for subsequent separation. During the process, unreacted material will be returned to the raw material intermediate tank, to be used as raw material for continued reaction. During the whole process, the FBR and the JFBR are coupled to the separating unit, thus forming an integrated multi-type reactors-separation system of higher efficiency, effectively shortening reaction time, reducing energy consumption, while reducing solid catalyst failure rate and extending catalyst service life.

The integrated system of this invention has the following advantages: (1) preliminary reaction of the material in FBR adopts one time passing, i.e. without cycles, thus reaction time is relatively short and energy consumption is relatively low; (2) resultant material of preliminary reaction enters the JFBR for intensified reaction, which can effectively shorten reaction time, reduce solid catalyst broken, and extend catalyst service life; (3) during the whole process, the reaction system formed by coupling of a FBR with a JFBR with a separation unit, so that the flow path and heat balance are more integrated, reaction time is greatly shortened, and process energy consumption is further lowered.

BRIEF DESCRIPTION

FIG. 1 is a schematic of the flow path of the process of this invention, wherein: R-1 is the FBR; R-2 is the JFBR; P-1, P-2, P-3, P-4, and P-5 are fluid pumps; V-1 is raw material intermediate storage tank; V-2 and V-5 are product intermediate storage tanks; V-3 is liquid-solid separation tank; V-4 is phase separator; F-1, F-2, F-3, F-4, F-5, F-6, F-7, F-8, and F-9 are valves; E-1, E-2, E-3, E-4, and E-5 are heat exchangers; FM-1, FM-2, FM-3, FM-4, and FM-5 are liquid flowmeters; T-1 is subsequent separation unit; 1, 2, 3, 4, 5, 6, 7, 8, 9, 10, 11, 12, 13, and 14 are pipelines; 15 is liquid discharge port; and 16 is sampling port.

DETAILED DESCRIPTION

This invention is further described by the following preferred embodiments. Preferred embodiment 1: production of 3000t/a of dihydromyrcenol using the process of this invention Refer to FIG. 1 for the process and operation steps of the integrated process. This system mainly comprises a reaction system formed by coupling of a FBR and a JFBR with a rectifying system, a phase separator, and an intermediate storage tank etc. Metering and control instruments and pipelines are provided among equipment. Liquid transfer pump P-1 is used to deliver dihydromyrcene hydration reaction raw materials of certain compounding ratio (mass ratio: dihydromyrcene/water/solvent=1:1:2, with solvent being dioxane) from raw material intermediate storage tank V-1 to the FBR R-1, via valve F-1, flowmeter FM-1, heat exchanger E-1 (where they are heated), and pipeline 3, for reaction. The FBR R-1 is filled with catalyst D72 (manufactured by Nankai University Catalyst Factory, same below). Filling capacity is $5m^3$, aspect ratio is 2:1, and reaction temperature is 110° C. After fresh raw materials pass the FBR R-1 once (residence time is 30 min), yield of dihydromyrcenol (wt %) is 5%. The resultant material is collected in intermediate buffer tank V-2, and then pumped by the liquid pump P-2 to pass valve F-3, flowmeter FM-2, heat exchanger E-2, and pipeline 5, and to enter the JFBR R-2 for intensified reaction. Volume of the JFBR is $4 m^3$, its mass ratio is 1.3:1, and 7 kg of catalyst D72 is suspended in this reactor. Samples are taken from sampling port 16 for analysis. When dihydromyrcenol reaches required concentration of 18%, the material will be delivered via pipeline 8, valve F-5, flowmeter FM-4, heat exchanger E-4, and pipeline 9, to enter phase separator V-4 for phase separation. The oil phase will enter buffer tank V-5 and be pumped by the liquid pump P-5 to pass valve F-9, flowmeter FM-5, heat exchanger E-5, and pipeline 12, and enter the separation unit T-1 for subsequent separation. Said separation unit T-1 is a packed column. After separation, dihydromyrcenol of purity of 98% will be obtained. Unreacted raw materials will be returned to raw material intermediate storage tank V-1 for reaction along with fresh materials. By means of the process of this invention, energy consumption is lowered by 28% as compared with traditional process.

Preferred embodiment 2: production of 5000t/a of terpineol using the process of this invention Operation method is the same as that of preferred embodiment 1. The liquid pump P-1 is used to deliver turpentine hydration raw materials of certain compounding ratio (mass ratio: turpentine/water/solvent=1:1:2, with solvent being isopropyl alcohol) from raw material intermediate storage tank V-1 to the FBR R-1, via valve F-1, flowmeter FM-1, heat exchanger E-1 (where the materials are heated), and pipeline 3, for reaction. The FBR R-1 is filled with wet type catalyst Amberlyst 15 (Amberlyst 15 is provided by Rohm & Haas of USA, same below). Filling capacity is $7 m^3$, aspect ratio is 2:1, and reaction temperature is 75° C. After fresh raw materials pass the FBR R-1 once (residence time is 30 min), yield of terpineol is 7%. The resultant material is collected in intermediate buffer tank V-2, and then pumped by the liquid pump P-2 to pass valve F-3, flowmeter FM-2, heat exchanger E-2, and pipeline 5, and to enter the JFBR R-2 for intensified reaction. Volume of the JFBR is 4.5 m$^3$ and its aspect ratio is 1.3:1. 8kg of wet type catalyst Amberlyst 15 is suspended in the JFBR. Samples are taken from sampling port 16 for analysis. When terpineol reaches required concentration of 22.8%, the material will be delivered via pipeline 8, valve F-5, flowmeter FM-4, heat exchanger E-4, and pipeline 9, to enter phase separator V-4 for phase separation. The oil phase will enter buffer tank V-5 and be pumped by the liquid pump P-5 to pass valve F-9, flowmeter FM-5, heat exchanger E-5, and pipeline 12, and enter the separation unit T-1 for subsequent separation. Said separation unit T-1 is a sieve-plate column. After separation, terpineol of purity of 98.5% will be obtained. Unreacted raw materials will be returned to raw material intermediate storage tank V-1 for reaction along with fresh materials. By means of the process of this invention, energy consumption is lowered by 30% as compared with traditional process.

Preferred embodiment 3: production of 6000t/a of butyl acetate using the process of this invention Refer to FIG. 1 for the process and operation steps of the integrated process. This system mainly comprises a FBR, a JFBR, a separation unit, and an intermediate storage tank etc. Metering and control instruments and pipelines are provided among equipment. The liquid pump P-1 is used to deliver acetic acid and n-butyl alcohol of a certain mass ratio (acetic acid/n-butyl alcohol=1:1) from raw material intermediate storage tank V-1 to the FBR R-1, via valve F-1, flowmeter FM-1, heat exchanger E-1 (where they are heated), and pipeline 3, for reaction. The FBR R-1 is filled with dry type catalyst Amberlyst 15 (dry type Amberlyst 15 is provided by Rohm & Haas of USA). Filling capacity is 5 m$^3$ and aspect ratio is 2:1. Water separator is installed. Reaction temperature is 100° C. After fresh raw materials pass the FBR R-1 once (residence time is 40 min), theoretical yield of n-butyl alcohol acetate is 12%. The resultant material is collected in intermediate buffer tank V-2, and then pumped by the liquid pump P-2 to pass valve F-3, flowmeter FM-2, heat exchanger E-2, and pipeline 5, and to enter the JFBR R-2 for the intensified reaction. Volume of the JFBR is 4 m$^3$ and its aspect ratio is 1.3:1. 10 kg of dry type catalyst Amberlyst 15 is suspended in this reactor. Samples are taken from sampling port 16 for analysis. When yield of butyl acetate reaches 78%, the material will be delivered via pipeline 8, flowmeter FM-4, heat exchanger E-4, and pipeline 11 to buffer tank V-5. This material will be pumped by the liquid pump P-5 to pass valve F-9, flowmeter FM-5, heat exchanger E-5, and pipeline 12, and enter the separation unit T-1 for subsequent separation. Said the separation unit T-1 is a valve trayed column. After separation, butyl acetate of purity of 99% will be obtained. Unreacted raw materials will be returned to raw material intermediate storage tank V-1 for reaction along with fresh materials. By means of the process of this invention, energy consumption is lowered by 34% as compared with traditional process.

Preferred embodiment 4: production of 8000t/a of acetic ether using the process of this invention The operation method is the same as that of preferred embodiment 3. The liquid pump P-1 is used to deliver acetic acid and ethanol of certain compounding ratio (acetic acid/ethanol =1:2) from raw material intermediate storage tank V-1 to the FBR R-1, via valve F-1, flowmeter FM-1, heat exchanger E-1 (where they are heated), and pipeline 3, for reaction. The FBR R-1 is filled by dry type catalyst D72. Filling capacity is 6 m$^3$ and aspect ratio is 2:1. Water separator is installed. Reaction temperature is 85° C. After fresh raw materials pass the FBR R-1 once (residence time is 45 min), yield of acetic ethanol is 14%. The resultant material is collected in intermediate buffer tank V-2, and then pumped by the liquid pump P-2 to pass valve F-3, flowmeter FM-2, heat exchanger E-2, and pipeline 5, and to enter the JFBR R-2 for intensified reaction. Volume of the JFBR is 4.5 m$^3$ and its aspect ratio is 1.25:1. 12 kg of dry type catalyst D72 is suspended in this reactor. Samples are taken from sampling port 16 for analysis. When concentration of acetic ether reaches 81%, the material will be delivered via pipeline 8, flowmeter FM-4, heat exchanger E-4, valve F-6, and pipeline 11, to enter buffer tank V-5. This material will be pumped by the liquid pump P-5 to pass valve F-9, flowmeter FM-5, heat exchanger E-5, and pipeline 12, and enter the separation unit T-1 for the subsequent separation. Said the separation unit T-1 is a packed column. After separation, acetic ether of purity of 99.4% will be obtained. Unreacted raw materials will be returned to raw material intermediate storage tank V-1 for reaction along with fresh materials. By means of the new process of this invention, energy consumption is lowered by 41% as compared with traditional process.

The invention claimed is:

1. An integrated process for producing a fluid product comprising the following steps:
    inputting raw materials of dihydromyrcene, water and solvent into an intermediate material storage tank via a first pipeline in a ratio of 1:1:2 by mass;
    heating the raw materials by a first heat exchanger;
    delivering the raw materials by a raw material pump via a first valve, a firs flow meter and a second pipeline to a fixed bed reactor filled with a solid catalyst comprised of a macroporous strongly acidic cation exchange resin the height and the degree of finish of which is determined according to a particular processing capacity and required residence time, for a preliminary reaction resulting in the formation of a reacted mixture, wherein the reacted mixture is sent to the fixed bed reactor one time and are collected by an intermediate buffer tank;
    delivering, by a material pump, the reacted mixture of the preliminary reaction in the fixed bed reactor from the intermediate buffer tank to a jet floating bed reactor, via a second valve, a second flow meter, a second heat exchanger and a third pipeline, for an intensified reaction, the jet floating bed reactor system comprising a reactor main body, a fluid pump, a third flow meter, a third heat exchanger, and a jet, wherein fluid from the jet floating bed reactor is pumped by the fluid pump through a third valve, the third flow meter, and heating the reacted mixture by the third heat exchanger to the temperature required by reaction, and then inputting the fluid into the jet through a fourth pipeline, wherein the fluid is injected into the jet floating bed reactor for a cyclic intensified reaction resulting in a fluid product of dihydromyrcenol;
    sampling, from a sampling port for analysis, the fluid product of dihydromyrcenol and when the fluid product reaches a specified concentration, outputting the fluid product via a fifth pipeline or a sixth pipeline, whereupon if a liquid phase of the fluid product is delaminated, the fluid product passes through a fourth flow meter, a fourth heat exchanger, a fourth valve, and the fifth pipeline to enter a phase separator for phase separation, and an upper layer oil phase liquid of the fluid products enters the intermediate buffer tank via the sixth pipeline;
    separating in the phase separator, the delaminated liquid phase into an oil layer and a water layer;

pumping the layer of the liquid phase without fluid product into the intermediate material storage tank via a seventh pipeline by a liquid pump;

pumping the layer of the liquid phase containing fluid product into the intermediate buffer tank by a second liquid pump, through a fifth valve, a fifth flow meter, heating the liquid phase by a fifth heat exchanger and then delivering the liquid phase containing fluid products to a subsequent separation system through a seventh pipeline for separation; and separating, in the subsequent separation system, fluid products and unreacted raw materials; and collecting the dihydromyrcenol fluid products, and pumping the unreacted raw materials back to the intermediate material storage tank for recycling.

2. The integrated process according to claim 1, wherein the subsequent separation system is a packing-type distillation column or a plate-type distillation column.

3. An integrated process for producing a fluid product comprising the following steps:

inputting raw materials of turpentine, water and solvent into an intermediate material storage tank via a first pipeline in a ratio of 1:1:2 by mass;

heating the raw materials by a first heat exchanger;

delivering the raw materials by a raw material pump via a first valve, a first flow meter and a second pipeline to a fixed bed reactor filled with a solid catalyst comprised of a macroporous strongly acidic cation exchange resin the height and the degree of finish of which is determined according to a particular processing capacity and required residence time, for a preliminary reaction resulting in the formation of a reacted mixture, wherein the reacted mixture is sent to the fixed bed reactor one time and are collected by an intermediate buffer tank;

delivering, by a material pump, the reacted mixture of the preliminary reaction in the fixed bed reactor from the intermediate buffer tank to a jet floating bed reactor, via a second valve, a second flow meter, a second heat exchanger and a third pipeline, for an intensified reaction, the jet floating bed reactor system comprising a reactor main body, a fluid pump, a third flow meter, a third heat exchanger, and a jet, wherein fluid from the jet floating bed reactor is pumped by the fluid pump through a third valve, the third flow meter, and heating the reacted mixture by the third heat exchanger to the temperature required by reaction, and then inputting the fluid into the jet through a fourth pipeline, wherein the fluid is injected into the jet floating bed reactor for a cyclic intensified reaction resulting in a fluid product of terpilenol;

sampling, from a sampling port for analysis, the fluid product of terpilenol and when the fluid product reaches a specified concentration, outputting the fluid product via a fifth pipeline or a sixth pipeline, whereupon if a liquid phase of the fluid product is delaminated, the fluid product passes through a fourth flow meter, a fourth heat exchanger, a fourth valve, and the fifth pipeline to enter a phase separator for phase separation, and an upper layer oil phase liquid of the fluid products enters the intermediate buffer tank via the sixth pipeline;

separating in the phase separator, the delaminated liquid phase into an oil layer and a water layer;

pumping the layer of the liquid phase without fluid product into the intermediate material storage tank via a seventh pipeline by a liquid pump;

pumping the layer of the liquid phase containing fluid product into the intermediate buffer tank by a second liquid pump, through a fifth valve, a fifth flow meter, heating the liquid phase by a fifth heat exchanger and then delivering the liquid phase containing fluid products to a subsequent separation system through a seventh pipeline for separation; and separating, in the subsequent separation system, fluid products and unreacted raw materials; and collecting the terpilenol fluid products, and pumping unreacted raw materials back into the intermediate material storage tank for recycling.

4. The integrated process according to claim 3, wherein the subsequent separation system is a packing-type distillation column or a plate-type distillation column.

5. An integrated process for producing a fluid product comprising the following steps:

inputting raw materials of acetic acid and butanol in a 1:1 ratio by mass or acetic acid and ethanol in a ratio of 1:2 by mass, into an intermediate material storage tank via a first pipeline;

heating the raw materials by a first heat exchanger;

delivering the raw materials by a raw material pump via a first valve, a first flow meter and a second pipeline to a fixed bed reactor filled with a solid catalyst comprised of a macroporous strongly acidic cation exchange resin the height and the degree of finish of which is determined according to a particular processing capacity and required residence time, for a preliminary reaction resulting in the formation of a reacted mixture, wherein the reacted mixture is sent to the fixed bed reactor one time and are collected by an intermediate buffer tank;

delivering, by a material pump, the reacted mixture of the preliminary reaction in the fixed bed reactor from the intermediate buffer tank to a jet floating bed reactor, via a second valve, a second flow meter, a second heat exchanger and a third pipeline, for an intensified reaction, the jet floating bed reactor system comprising a reactor main body, a fluid pump, a third flow meter, a third heat exchanger, and a jet, wherein fluid from the jet floating bed reactor is pumped by the fluid pump through a third valve, the third flow meter, and heating the reacted mixture by the third heat exchanger to the temperature required by reaction, and then inputting the fluid into the jet through a fourth pipeline, wherein the fluid is injected into the jet floating bed reactor for a cyclic intensified reaction resulting in a fluid product of butyl acetate or ethyl acetate;

sampling, from a sampling port for analysis, the fluid product of butyl acetate or ethyl acetate and when the fluid product reaches a specified concentration, outputting the fluid product via a fifth pipeline or a sixth pipeline, whereupon if a liquid phase of the fluid product is delaminated, the fluid product passes through a fourth flow meter, a fourth heat exchanger, a fourth valve, and the fifth pipeline to enter a phase separator for phase separation, and an upper layer oil phase liquid of the fluid products enters the intermediate buffer tank via the sixth pipeline;

separating in the phase separator, the delaminated liquid phase into an oil layer and a water layer;

pumping the layer of the liquid phase without fluid product into the intermediate material storage tank via a seventh pipeline by a liquid pump;

pumping the layer of the liquid phase containing fluid product into the intermediate buffer tank by a second liquid pump, through a fifth valve, a fifth flow meter, heating the liquid phase by a fifth heat exchanger and then delivering the liquid phase containing fluid products to a subsequent separation system through a seventh pipeline for separation; and separating, in the subsequent separation system, fluid products and unreacted raw materials; and collecting the butyl acetate or ethyl acetate fluid products, and pumping unreacted raw materials back into the intermediate material storage tank for recycling.

6. The integrated process according to claim 5, wherein the subsequent separation system is a packing-type distillation column or a plate-type distillation column.

\* \* \* \* \*